US00PP31263P2

(12) United States Plant Patent
Eveleens

(10) Patent No.: US PP31,263 P2
(45) Date of Patent: Dec. 24, 2019

(54) ***HYDRANGEA* PLANT NAMED 'HORTMACARO'**

(50) Latin Name: *Hydrangea macrophylla*
Varietal Denomination: Hortmacaro

(71) Applicants: KOLSTER HOLDING B.V., Boskoop (NL); HORTEVE BREEDING B.V., Aalsmeer (NL)

(72) Inventor: Cornelis P. Eveleens, Aalsmeer (NL)

(73) Assignees: Kolster Holding B.V., Boskoop (NL); Horteve Breeding B.V., Aalsmeer (NL)

( * ) Notice: Subject to any disclaimer, the term of this patent is extended or adjusted under 35 U.S.C. 154(b) by 0 days.

(21) Appl. No.: 15/999,930

(22) Filed: Aug. 31, 2018

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
See application file for complete search history.

(56) References Cited

PUBLICATIONS

UPOV hit on *Hydrangea* plant named, 'Hortmacaro', QZ PBR 20180825, published Jun. 16, 2018.*

* cited by examiner

*Primary Examiner* — Anne Marie Grunberg
(74) *Attorney, Agent, or Firm* — C. A. Whealy

(57) ABSTRACT

A new and distinct cultivar of *Hydrangea* plant named 'Hortmacaro', characterized by its upright and spreading plant habit; moderately vigorous to vigorous growth habit and moderate growth rate; moderate branching habit with strong and thick sturdy stems; large mophead-type inflorescences with dark red purple-colored sterile flowers; and good postproduction longevity.

2 Drawing Sheets

Botanical designation: *Hydrangea macrophylla.*
Cultivar denomination: 'HORTMACARO'.

BACKGROUND OF THE INVENTION

The present invention relates to a new and distinct cultivar of *Hydrangea* plant, botanically known as *Hydrangea macrophylla*, commercially referred to as a mophead-type *Hydrangea* and hereinafter referred to by the name 'Hortmacaro'.

The new *Hydrangea* plant is a product of a planned breeding program conducted by the Inventor in Boskoop, The Netherlands. The objective of the breeding program was to create new *Hydrangea* plants with large inflorescences with numerous dark red purple-colored sterile flowers and good postproduction longevity.

The new *Hydrangea* plant originated from a cross-pollination made by the Inventor in May, 2009 in Boskoop, The Netherlands, of a proprietary selection of *Hydrangea macrophylla* identified as code number 07-071-02, not patented, as the female, or seed, parent with a proprietary selection of *Hydrangea macrophylla* identified as code number 08-025-01, not patented, as the male, or pollen, parent. The new *Hydrangea* plant was discovered and selected by the Inventor as a single flowering plant from within the progeny of the stated cross-pollination in a controlled greenhouse environment in Boskoop, The Netherlands in June, 2011.

Asexual reproduction of the new *Hydrangea* plant by vegetative terminal cuttings in a controlled environment in Boskoop, The Netherlands since 2011 has shown that the unique features of this new *Hydrangea* plant are stable and reproduced true to type in successive generations.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Hortmacaro'. These characteristics in combination distinguish 'Hortmacaro' as a new and distinct *Hydrangea* plant:

1. Upright and spreading plant habit.
2. Moderately vigorous to vigorous growth habit and moderate growth rate.
3. Moderate branching habit with strong and thick sturdy stems.
4. Large mophead-type inflorescences with dark red purple-colored sterile flowers.
5. Good postproduction longevity.

Plants of the new *Hydrangea* can be compared to plants of the female parent selection. Plants of the new *Hydrangea* differ primarily from plants of the female parent selection in sterile flower color as sterile flower sepals of plants of the new *Hydrangea* are lighter red purple in color than sterile flower sepals of plants of the female parent selection. In addition, margins of sterile flower sepals of plants of the new

*Hydrangea* are serrate and undulate whereas margins sterile flower sepals of plants of the female parent selection are entire and slightly undulate.

Plants of the new *Hydrangea* can be compared to plants of the male parent selection. Plants of the new *Hydrangea* differ primarily from plants of the male parent selection in branching habit as plants of the new *Hydrangea* are not as freely branching as plants of the male parent selection. In addition, margins of sterile flower sepals of plants of the new *Hydrangea* are serrate and undulate whereas margins sterile flower sepals of plants of the male parent selection are entire and slightly undulate.

Plants of the new *Hydrangea* can be compared to plants of the *Hydrangea macrophylla* 'Magical Opal', disclosed in U.S. Plant Pat. No. 20,483. In side-by-side comparisons plants of the new *Hydrangea* differ primarily from plants of 'Magical Opal' in the following characteristics:

1. Plants of the new *Hydrangea* are not as freely branching as plants of 'Magical Opal'.
2. Plants of the new *Hydrangea* have larger sterile flower sepals than plants of 'Magical Opal'.
3. Sterile flower sepals of plants of the new *Hydrangea* are curly and serrate whereas sterile flower sepals of plants of 'Magical Opal' are mostly flat with entire margins.

Plants of the new *Hydrangea* can be compared to plants of the *Hydrangea macrophylla* 'Magical Emerald', disclosed in U.S. Plant Pat. No. 20,464. In side-by-side comparisons plants of the new *Hydrangea* differ primarily from plants of 'Magical Emerald' in the following characteristics:

1. Plants of the new *Hydrangea* are more freely branching than plants of 'Magical Emerald'.
2. Plants of the new *Hydrangea* have darker red purple sterile flower sepals than plants of 'Magical Emerald'.
3. Sterile flower sepals of plants of the new *Hydrangea* are curly and serrate whereas sterile flower sepals of plants of 'Magical Emerald' are flat with entire margins.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet is a side perspective view of a typical flowering plant of 'Hortmacaro' grown in a container.

The photograph on the second sheet is a close-up view of a typical inflorescence of 'Hortmacaro'.

DETAILED BOTANICAL DESCRIPTION

Plants used in the aforementioned photographs and in the following description were grown during the summer in 17-cm containers in a glass-covered greenhouse in Boskoop, The Netherlands and under cultural practices typical of commercial *Hydrangea* production. During the production of the plants, day temperatures ranged from 16° C. to 30° C. and night temperatures ranged from 10° C. to 18° C. Plants of the new *Hydrangea* were two years old when the photographs and description were taken. Plants of the new *Hydrangea* are not typically treated with aluminum sulfate to "blue" the inflorescences. In the following description, color references are made to The Royal Horticultural Society Colour Chart, 2015 Edition, except where general terms of ordinary dictionary significance are used.

Botanical description: *Hydrangea macrophylla* 'Hortmacaro'.

Parentage:

*Female, or seed, parent.*—Proprietary selection of *Hydrangea macrophylla* identified as code number 07-071-02, not patented.

*Male, or pollen, parent.*—Proprietary selection of *Hydrangea macrophylla* identified as code number 08-025-01, not patented.

Propagation:

*Type cutting.*—By vegetative terminal cuttings.

*Time to initiate roots, summer.*—About three weeks at temperatures about 15° C. to 25° C.

*Time to produce a rooted young plant, summer.*—About six weeks at temperatures about 15° C. to 25° C.

*Root description.*—Medium in thickness, fibrous; typically creamy white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Upright and spreading plant habit; inverted triangle in shape; strong and sturdy lateral branches; moderate growth rate and moderately vigorous to vigorous growth habit.

*Plant height.*—About 47.2 cm.

*Plant diameter or area of spread.*—About 50 cm.

Lateral branch description:

*Branching habit.*—Moderate branching habit; when pinched, about five lateral branches develop per plant.

*Length.*—About 32.1 cm.

*Diameter.*—About 7.5 mm.

*Internode length.*—About 9.9 cm.

*Texture.*—Smooth, glabrous; fully developed, woody.

*Aspect.*—Upright to about 15° from vertical.

*Strength.*—Strong, sturdy.

*Color.*—When developing: Close to 144A. Developed: Close to 144A to 144B; at the internodes, tinged with close to N186C; when woody, close to N199A and N200B to N200C.

*Lenticels.*—Not observed.

Leaf description:

*Arrangement.*—Opposite, simple.

*Length.*—About 12.9 cm.

*Width.*—About 10.6 cm.

*Shape.*—Broadly ovate.

*Apex.*—Apiculate.

*Base.*—Short attenuate to somewhat obtuse.

*Margin.*—Coarsely serrate.

*Texture, upper surface.*—Smooth to slightly rugose, glabrous.

*Texture, lower surface.*—Smooth to moderately rugose, mostly glabrous, sparsely pubescent along venation.

*Venation pattern.*—Pinnate.

*Color.*—Developing leaves, upper surface: Darker than between 137A and 143A. Developing leaves, lower surface: Close to between 146B and 146C. Fully expanded leaves, upper surface: Close to 137A; venation, close to N148C. Fully expanded leaves, lower surface: Close to 146B; venation, close to 145C.

*Petioles*.—Length: About 2.3 cm. Diameter: About 4.5 mm. Texture and luster, upper surface: Smooth, glabrous; matte. Texture and luster, lower surface: Smooth, glabrous; slightly glossy. Color, upper surface: Close to 145B. Color, lower surface: Close to 144B.

Flower description:

*Flower type and habit*.—Showy sterile flowers and small inconspicuous fertile flowers arranged on mophead-type terminal panicles; panicles flattened globular in shape; fertile flowers face mostly upright and sterile flowers face upright to outwardly to slightly drooping depending on their position in the inflorescence.

*Fragrance*.—None detected.

*Natural flowering season*.—Plants flower from late spring to late summer in The Netherlands.

*Flower longevity*.—Fertile flowers last about five days on the plant, fertile flowers not persistent; sterile flowers last about six weeks on the plant, sterile flowers persistent.

*Quantity of flowers*.—Freely flowering habit; about 40 fertile flowers per panicle and about 85 sterile flowers per panicle.

*Panicle height*.—About 10.4 cm.

*Panicle diameter*.—About 17.1 cm.

*Fertile flower buds*.—Length: About 4 mm. Diameter: About 5 mm. Shape: Flattened globular. Color: Close to 69D and 70B to 70C; fading towards the base, close to 145D; at the base, close to 150B.

*Sterile flower buds*.—Length: About 1.4 cm. Diameter: About 1 cm. Shape: Cup-shaped. Color: Close to 63B.

*Fertile flower diameter*.—About 9 mm.

*Fertile flower depth* (*height*).—About 7 mm.

*Sterile flower diameter*.—About 5.8 cm.

*Sterile flower depth* (*height*).—About 2.3 cm.

*Petals, fertile flowers*.—Quantity and arrangement: Six in a single whorl. Length: About 4 mm. Width: About 2 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to 65A to 65B; color does not fade with development. When opening and fully opened, lower surface: Close to 65A; color does not change with development.

*Petals, sterile flowers*.—Quantity and arrangement: About four in a single whorl. Length: About 4 mm. Width: About 3 mm. Shape: Ovate, concave. Apex: Acute. Base: Cuneate. Margin: Entire. Texture and luster, upper surface: Smooth, glabrous; slightly glossy. Texture and luster, lower surface: Smooth, glabrous; matte. Color: When opening and fully opened, upper surface: Close to 65A to 65B; color does not fade with development. When opening and fully opened, lower surface: Close to 65A; color does not change with development.

*Sepals, fertile flowers*.—Quantity and arrangement: About six in a single whorl. Length: About 2 mm. Width: About 1.5 mm. Shape: Ovate. Apex: Acute. Base: Broadly cuneate. Margin: Entire. Texture and luster, upper surface: Smooth, glabrous; matte. Texture and luster, lower surface: Smooth, glabrous; slightly glossy. Color: When opening and fully opened, upper surface: Close to 150B; fading towards the base to close to 145D; color does not change with development. When opening and fully opened, lower surface: Close to 150B; fading towards the base to close to 145D; color does not change with development.

*Sepals, sterile flowers*.—Quantity and arrangement: Four or occasionally five in a single whorl. Length: About 3.2 cm. Width: About 3.8 cm. Shape: Broadly reniform to reniform. Apex: Broadly and bluntly apiculate. Base: Cuneate. Margin: Irregularly and coarsely crenate to serrate; moderately to strongly undulate. Texture and luster, upper and lower surfaces: Smooth, glabrous; matte. Color: When opening, upper surface: Close to 63A. When opening, lower surface: Close to 63C. Fully opened, upper surface: Close to 64D; color does not fade with development. Fully opened, lower surface: Close to 65A; color does not fade with development.

*Pedicels, fertile flowers*.—Length: About 2 mm. Diameter: About 1 mm. Strength: Moderately strong. Aspect: Mostly upright, about 10° from vertical. Texture and luster: Sparsely pubescent; matte. Color: Close to 150D slightly tinged with close to 63D.

*Pedicels, sterile flowers*.—Length: About 1.9 cm. Diameter: About 2 mm. Strength: Moderately strong. Aspect: About 35° from vertical. Texture and luster: Moderately pubescent; matte. Color: Close to between 63C and 64D.

*Reproductive organs, fertile flowers*.—Stamens: Quantity per flower: About twelve. Filament length: About 3 mm. Filament color: Close to NN155D. Anther length: About 1.5 mm. Anther shape: Oblong. Anther color: Close to 155C. Pollen amount: Moderate. Pollen color: Close to 160C. Pistils: Pistil quantity per flower: About three or occasionally two. Pistil length: About 1.5 mm. Stigma shape: Club-shaped. Stigma color: Close to NN155A. Style length: About 0.5 mm. Style color: Close to NN155A. Ovary color: Close to N155A.

*Reproductive organs, sterile flowers*.—Stamens: Quantity per flower: About eight. Filament length: About 2 mm. Filament color: Close to NN155B. Anther length: About 1.5 mm. Anther shape: Broadly oblong. Anther color: Close to 155C. Pollen amount: Moderate. Pollen color: Close to 160C. Pistils: Pistil quantity per flower: About three. Pistil length: About 1.5 mm. Stigma shape: Club-shaped. Stigma color: Close to NN155A. Style length: About 0.5 mm. Style color: Close to NN155A. Ovary color: Close to N155A.

*Seeds*.—To date, seed development has not been observed on plants of the new *Hydrangea*.

Disease & pest resistance: Under commercial production conditions, plants of the new *Hydrangea* have not been observed to be resistant to pathogens and pests common to *Hydrangea* plants.

Temperature tolerance: Plants of the new *Hydrangea* have been shown to be suitable for USDA Hardiness Zones 5 to 9.

It is claimed:

1. A new and distinct *Hydrangea* plant named 'Hortmacaro' as illustrated and described.

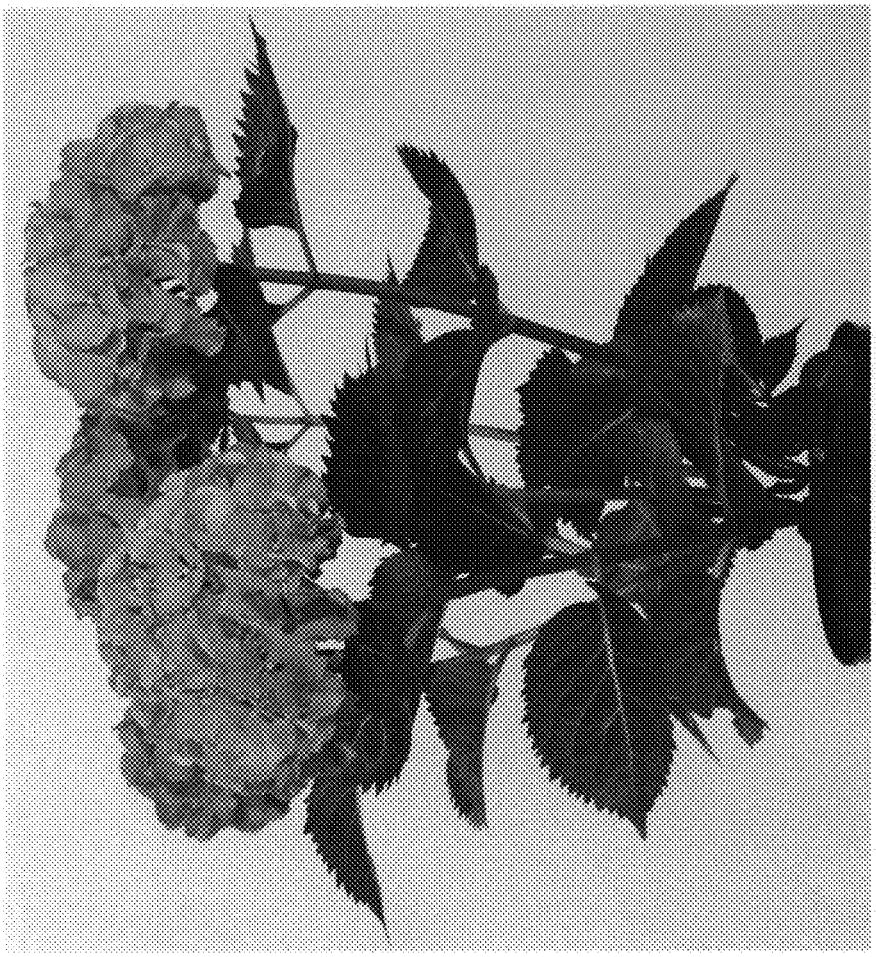

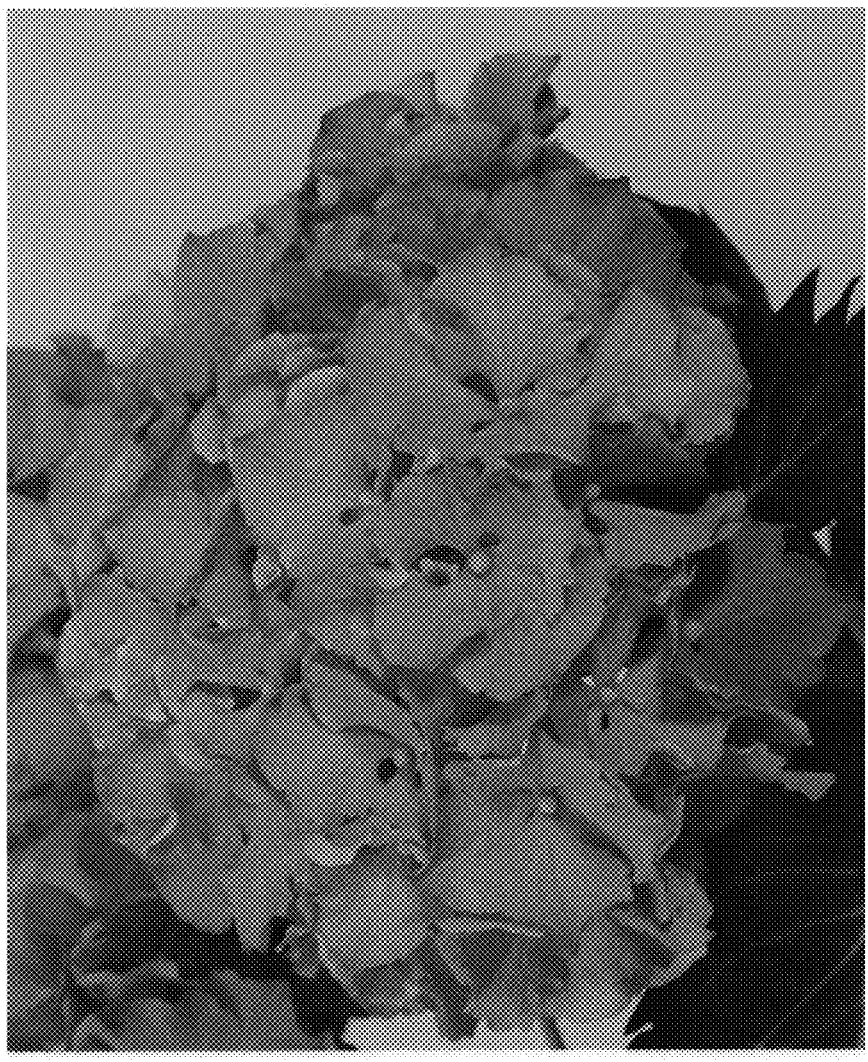

* * * * *